US012648842B2

(12) United States Patent
Weigel et al.

(10) Patent No.: US 12,648,842 B2
(45) Date of Patent: Jun. 9, 2026

(54) ESTABLISHING A PHYSIOLOGICAL SKIN-MATERIAL CONNECTION

(71) Applicant: FRAUNHOFER-GESELLSCHAFT ZUR FÖRDERUNG DER ANGEWANDTEN FORSCHUNG E.V., Munich (DE)

(72) Inventors: Tobias Weigel, Würzburg (DE); Bastian Christ, Würzburg (DE); Jörn Probst, Würzburg (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 882 days.

(21) Appl. No.: 17/923,805

(22) PCT Filed: May 5, 2021

(86) PCT No.: PCT/EP2021/061829
§ 371 (c)(1),
(2) Date: Nov. 7, 2022

(87) PCT Pub. No.: WO2021/224321
PCT Pub. Date: Nov. 11, 2021

(65) Prior Publication Data
US 2024/0024090 A1      Jan. 25, 2024

(30) Foreign Application Priority Data
May 8, 2020      (DE) ..................... 10 2020 205 823.7

(51) Int. Cl.
*A61F 2/10*           (2006.01)

(52) U.S. Cl.
CPC ........ *A61F 2/105* (2013.01); *A61F 2220/005* (2013.01); *A61F 2230/0063* (2013.01); *A61F 2310/00377* (2013.01)

(58) Field of Classification Search
CPC ................ A61F 2/105; A61F 2220/005; A61F 2230/0063; A61F 2310/00377
See application file for complete search history.

(56) References Cited

U.S. PATENT DOCUMENTS

2019/0328935 A1* 10/2019 Kang ........................ A61P 9/00
2024/0024090 A1* 1/2024 Weigel ................... A61L 29/16

FOREIGN PATENT DOCUMENTS

DE          19529036 A1      3/1997
DE          19728489 A1      1/1999
(Continued)

OTHER PUBLICATIONS

International Preliminary Report on Patentability for PCT/EP2021/061829 dated Nov. 17, 2022, 8 pages.
(Continued)

*Primary Examiner* — Seema Mathew
(74) *Attorney, Agent, or Firm* — Sheppard Mullin Richter & Hampton LLP

(57) ABSTRACT
The present invention relates to an implant comprising at least one three-dimensional porous structural element of at least one synthetic polymer, wherein the at least one porous structural element is irreversibly attached to an implant element by means of at least one adhesive polymer, methods for preparing the same, and uses thereof.

15 Claims, 6 Drawing Sheets

(56)     References Cited

FOREIGN PATENT DOCUMENTS

Figure 1:
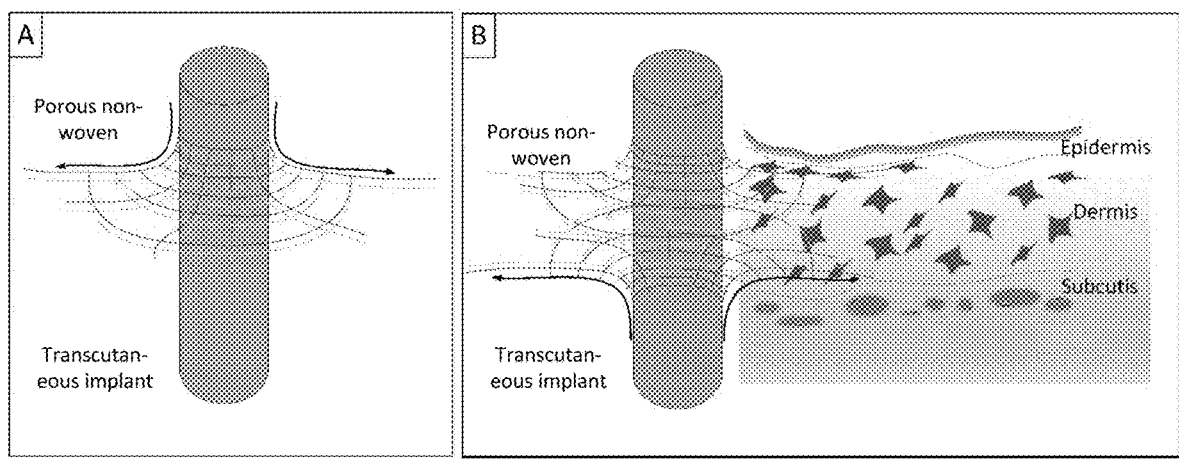

DE      102005054940  A1      5/2007
WO      WO-2015049524  A1  *   4/2015   ............. A61L 27/56

OTHER PUBLICATIONS

International Search Report and Written Opinion for PCT/EP2021/061829 dated Jul. 28, 2021, 15 pages, English translation of ISR only.

Milleret et al. Tuning electrospinning parameters for production of 3D-fiber-fleeces with increased porosity for soft tissue engineering applications. European Cell and Materials. 2011; 21:286-303.

* cited by examiner

ESTABLISHING A PHYSIOLOGICAL SKIN-MATERIAL CONNECTION

This application is a U.S. National Stage Application under 35 U.S.C. 371 of International Application No. PCT/EP2021/061829, filed Mar. 5, 2021, which claims priority to German Patent Application 10 2020 205 823.7, filed on May 8, 2020. The contents of each of the which are hereby incorporated by reference in their entirety into the present disclosure.

The present invention relates to an implant comprising at least one three-dimensional porous structural element of at least one synthetic polymer, wherein the at least one porous structural element is irreversibly attached to an implant element by means of at least one adhesive polymer, methods for preparing the same, and uses thereof.

The skin represents a natural barrier and protects the body from external environmental influences such as rain and UV rays, but also from pathogens and chemical substances. If this skin barrier is damaged, pathogens, for example bacteria, can easily penetrate the body and multiply there. The skin barrier is also damaged by transcutaneous implants such as catheters or external fixators for healing complicated bone fractures. Implant materials always trigger a foreign body reaction in the body, which varies in severity depending on the patient and the material. Therefore, the implant material is never completely enclosed by the skin. As a result, germs nest between the implant material and the human tissue. Transcutaneous implants, especially at the transcutaneous stoma, must therefore always be cleaned, thus causing high costs in the area of patient care and often leading to severe courses of disease due to bacteria.

Strategies to prevent germination of the implant, especially in the area of the stoma, are urgently needed. The high demand is shown by the large number of transcutaneous implants that penetrate the skin barrier for several weeks, months or even for life. Patients whose therapy phase lasts for several weeks or months are often supplied with artificial accesses. Examples include tracheatomy, percutaneous endoscopic gastrostomy or catheters (for example, a PICC catheter).

Long-term applications serve the purpose of improving the quality of life of patients for as long as possible. These include implants such as bone conduction hearing apparatuses, transcutaneous osseointegrated prosthesis systems or CAPD catheters for peritoneal dialysis. Other applications such as a retroauricular fixed port for haemodialysis are under development.

With all these transcutaneous implants, there is a risk of bacterial infections, some of which are life-threatening, and which often lead to the loss of the implant and a necessary revision operation.

Therefore, solutions are being sought to bind the dermal tissue to transcutaneous implants in a mechanically resilient and bacteria-tight way.

The challenge to prevent an infection at the transcutaneous implant lies in the realisation of a permanently mechanically resilient connection between implant and attached cutaneous tissue.

DE 195 290 36 A1 describes a composite material comprising a collagen felt, usable for the preparation of composite materials and implants.

DE 197 28 489 A1 describes a felt-like collagen nanofibre non-woven which is attached to an implant by adhesion.

WO2011/147409 A3 describes endoprostheses obtained by electrospinning nanofibres onto the surface of a metallic implant.

The present invention is therefore based on the technical problem of providing means and methods that overcome problems and disadvantages discussed above. In particular, the present invention is based on the technical problem of providing an implant and a method for preparing an implant which allows an advantageous attachment between the implant and the adjacent tissue and, in particular, to prevent bacteria from migrating and/or germination of the implant-tissue interface, in particular to allow the implant to grow into the surrounding tissue as naturally as possible.

The present invention is also based on the technical problem of providing a method for preparing such an implant.

The present invention solves the problem underlying it by providing the teachings of the independent claims.

Accordingly, the present invention provides an implant comprising at least one three-dimensional porous structural element of at least one synthetic polymer, wherein the at least one porous structural element is irreversibly attached to an implant element by means of at least one adhesive polymer.

In a particularly preferred embodiment of the present invention, the three-dimensional porous structural element is made of at least one synthetic polymer selected from the group consisting of electrospun porous non-woven of nanofibres of at least one synthetic fibre polymer, porous sponge, porous membrane and foamed porous polymer.

In a particularly preferred embodiment of the present invention, the three-dimensional porous structural element of at least one synthetic polymer is an electrospun porous non-woven of nanofibres of at least one synthetic fibre polymer.

Accordingly, in a preferred embodiment, the present invention provides an implant comprising at least one electrospun porous non-woven of nanofibres of at least one synthetic fibre polymer, wherein the at least one porous non-woven is irreversibly attached to an implant element by means of at least one adhesive polymer.

Advantageously, the present invention provides a mechanically particularly resilient and bacteria-tight attachment between surrounding tissue and implant. The implant according to the invention makes it possible to attach an implant element to the surrounding tissue of the implant element via the at least one porous structural element, in particular electrospun porous non-woven, which is irreversibly, i.e. permanently, attached to the implant element according to the invention. The at least one porous structural element irreversibly attached to the implant element according to the invention, in particular electrospun non-woven, is porous, i.e. has pores, and in an optional embodiment can be colonised with cells in vitro, in vivo or in vitro and in vivo. After integration into the implant site, the implant according to the invention allows the implant element to grow into the implant site as naturally as possible, corresponding to physiological natural processes, whereby a foreign body reaction is minimised as far as possible and the surrounding tissue, in particular skin tissue, can grow tightly and mechanically resiliently onto the implant element. The porous structure of the at least one porous structural element, in particular porous non-woven, provided according to the invention, permits cell colonisation in vitro and/or in vivo and thus creates a tissue structure in the immediate vicinity of the implant element which is as close as possible to natural tissue, wherein, in addition, a mechanically highly stable bacteria-tight attachment is created via the irreversible adhesive-polymer-mediated bond of the at least one porous structural element, in particular electrospun porous non-woven, to the implant element. The porous structure of the at least one porous structural element, in particular electrospun porous non-woven, provided according to the invention, enables the implant element to grow directly into the surrounding tissue. In addition, the method according to the invention allows the implant element material, which may be foreign to the body, in particular artificial material, to be shielded from the body by using the at least one porous structural element, in particular electrospun porous non-woven, which is as physiologically constructed as possible, thus reducing or avoiding possible foreign body reactions, but at the same time allowing the implant element to be integrated into the tissue in a physiologically and mechanically resilient manner.

The present invention is therefore advantageous in that it enables a permanently mechanically resilient attachment between the implant and the adjacent tissue, in particular cutaneous tissue. Advantageously, the invention enables the tissue, in particular the cutaneous tissue, to seal with the implant in a bacteria-tight manner and, in an advantageous manner, physiological processes of the surrounding tissue, in particular the skin, are not disturbed, so that regular regeneration of the surrounding tissue, in particular the skin, is enabled.

According to the invention, the synthetic polymers, in particular fibre polymers, can be prepared using conventional electrospinnable and water- and possibly ethanol-insoluble materials. PCL and polyamide 6 are particularly preferred and in particular suitable for a skin model material (FIG. 2B), indicating the particular suitability of the polyesters and polyamides. Furthermore, inorganic-organic hybrid materials, in particular based on organically modified silanes, poly(hydroxyethoxy)cyclosiloxanes and titanium-oxo-carboxo complexes, can also be used.

Preferably, mixtures of the synthetic polymers, in particular inorganic-organic hybrid materials with organic polymers, can also be used.

In a preferred embodiment according to the invention, the at least one synthetic polymer, in particular synthetic fibre polymer, is selected from the group consisting of polyester, polyether, polyamide, polyamine, polyacrylonitrile, polyolefins, polypeptide, polypeptoid, polysaccharide, polyoxazoline and inorganic-organic hybrid material.

In a particularly preferred embodiment, an inorganic-organic hybrid material that can be used as a synthetic polymer, in particular a synthetic fibre polymer, is an organic-modified silane, a poly(hydroxyethoxy)cyclosiloxane or a titanium-oxo-carboxo complex.

In a particularly preferred embodiment, the at least one synthetic polymer, in particular synthetic fibre polymer, is a polyester, in particular PCL (polycaprolactone).

In a particularly preferred embodiment, the at least one synthetic polymer, in particular synthetic fibre polymer, is a polyamide, in particular PA6.

In a particularly preferred embodiment of the present invention, the at least one synthetic polymer, in particular synthetic fibre polymer, may be a biodegradable polymer, in particular fibre polymer.

In a particularly preferred embodiment of the present invention, the at least one synthetic polymer, in particular synthetic fibre polymer, may be a permanently stable and/or non-biodegradable polymer, in particular fibre polymer.

In a particularly preferred embodiment, the at least one synthetic polymer, in particular the synthetic fibre polymer, may have an antiprofilerative, anti-inflammatory, antimigrative, antiphlogistic, antiangiogenic, cytostatic, antirestenotic, antineoplastic, antibacterial and/or antifungal effect, in particular antibiotic effect.

In a preferred embodiment according to the invention, the at least one adhesive polymer is a crosslinked or non-crosslinked polymer, in particular a crosslinked or non-crosslinked poly-hydroxyethyl methacrylate (poly-HEMA) polymerised [2-(methacryloyloxy)ethyl]trimethylammonium chloride (METAC), polymerised 2-aminoethyl methacrylate (AEMA) or a copolymer of at least two of the monomers built up from HEMA, METAC or AEMA.

In a particularly preferred embodiment, the adhesive polymer is a copolymer prepared from HEMA and METAC, in particular prepared from a 10 to 1 blend of HEMA and METAC (based on wt. %).

In a particularly preferred embodiment, the at least one adhesive polymer can have an antiprofilerative, anti-inflammatory, antimigrative, antiphlogistic, antiangiogenic, cytostatic, antirestentotic, antineoplastic, antibacterial and/or antifungal, in particular antibiotic, activity. Particularly preferred adhesive polymers exhibiting such activity are cationic polymers, in particular polymers which have primary amines or quaternary ammonium units in their side chain.

In a preferred embodiment according to the invention, the pore size of the porous structural element, in particular electrospun porous non-woven, is 0.1 µm to 800 µm, in particular 0.1 µm to 300 µm, in particular 0.5 µm to 100 µm.

As a measuring method of the pores with regard to the pore sizes and the pore volume, investigations by means of microscopic images, in particular light microscopes, scanning electron microscopy or confocal microscopy, serve. The porous structural element can be fixed in an embedding material beforehand, in particular paraffin, ice or resin, and thin sections can then be generated. In particular, the determination of the pore size and the pore volume is carried out with a confocal microscope, in particular by means of confocal reflection microscopy, especially at a temperature of 20 to 25° C., in particular 20° C.

In a preferred embodiment according to the invention, the porous structural element, in particular electrospun porous non-woven, has a thickness of 50 µm to 300 µm, in particular 100 µm to 250 µm, in particular 150 µm to 250 µm.

In a preferred embodiment according to the invention, the implant element is composed of an organic material, an inorganic material or an organic-inorganic hybrid material, in particular of plastic, metal and/or a metal compound.

In a particularly preferred embodiment, the implant element may be composed of at least one metal and/or at least one metal compound, in particular TiN (titanium nitride).

In a particularly preferred embodiment of the present invention, the implant element may be composed of at least one metal and/or at least one metal compound and may be coated with polymers or carbon layers, in particular diamond-like carbon layers, for example Diamond like Carbon (DLC).

In a particularly preferred embodiment, the implant element may in particular be an implant element made of plastic or/and metal-coated plastic.

In a particularly preferred embodiment of the present invention, the implant element may be established of plastic and coated with polymers or/and carbon layers, in particular diamond-like carbon layers, for example DLC.

In a preferred embodiment according to the present invention, the porous structural element, in particular electrospun porous non-woven, is cell-free.

In a particularly preferred embodiment of the present invention, the implant element may be irreversibly attached to at least one, in particular one or more than one, in particular two, three, four, five, six, seven, eight, nine, ten, in particular eleven identical or different porous three-dimensional structural elements, in particular electrospun porous non-woven, in each case, in particular at least partially laminar attached.

In a preferred embodiment according to the invention, the implant, in particular the porous structural element, in particular electrospun porous non-woven fibres, has cells of at least one cell type, in particular human or animal cells, in particular human cells. The cells may in particular be autologous or allogeneic cells.

The cells of at least one cell type present in the implant according to the invention, in particular porous structural element, in particular electrospun porous non-woven, can be introduced into the implant provided according to the invention in vitro, that is ex vivo, in particular by seeding and cultivating. In another embodiment, the implant provided according to the invention can be implanted in the body without cells being provided and then serve there as a substrate for ingrowth of the body's own cells or at least introduced, for example sprayed-in, cells in vivo.

In a preferred embodiment according to the invention, the porous structural element, in particular electrospun porous non-woven, has in particular dermal fibroblasts and/or keratinocytes, in particular human dermal fibroblasts and/or human keratinocytes.

In a preferred embodiment according to the invention, the implant, in particular the porous structural element, in particular electrospun porous non-woven, of the present invention has cells of at least two different cell types. In a particularly preferred embodiment, the implant has cells of at least two different cell types, in particular cells of at least three different cell types, the cells preferably being in the form of tissues, in particular tissue layers, in particular epidermal or subepidermal tissue layers. This enables tissue- and/or cell-specific individualisation of the implant according to the invention, so that it can be specifically adapted to an implantation site prior to implantation at or in that site.

In a particularly preferred embodiment, the at least two cells present in the implant, in particular the porous structural element, in particular the electrospun porous non-woven, in particular present in the form of one or more tissues, may be present in an extracellular matrix, in particular one that has formed after seeding and cultivating the cells on the porous structural element.

In a particularly preferred embodiment, an implant is provided which is suitable for implantation into the skin and, in a preferred embodiment, has dermal fibroblasts and/or keratinocytes.

In a particularly preferred embodiment of the invention, the implant may also be suitable for implantation into other implant sites, in particular epithelial or endothelial tissue, in particular for implantation into the mucosa, trachea, stomach, intestine, bladder or vessels.

In a preferred embodiment, for forming the implant for the epithelial or endothelial tissue, corresponding epithelial- or endothelial-specific cell types are introduced into the implant provided according to the invention, in particular porous structural element, in particular electrospun porous non-woven, in particular by seeding the cells into the porous structural element and cultivating them in vitro.

In a particularly preferred embodiment, the present implant is a transcutaneous implant, in particular a whole skin model, in particular a three-dimensional whole skin model.

In a preferred embodiment according to the invention, the implant, in particular the porous structural element, in particular electrospun porous non-woven, and/or the at least one adhesive polymer has at least one active agent, in particular an antibiotic active agent.

In a particularly preferred embodiment, the active agent has an antiproliferative, anti-inflammatory, antimigrative, antiphlogistic, antiangiogenic, cytostatic, antirestenotic, antineoplastic, antibacterial and/or antifungal effect. Preferably, the agent ingredient is in particular streptomycin, penicillin, vancomycin or gentamycin.

In a preferred embodiment according to the invention, the electrospun porous non-woven can be produced by
  i) providing at least one porogen and at least one synthetic fibre polymer,
  ii) electrospinning the at least one fibre polymer while adding the at least one porogen to obtain an electrospun porogen-containing non-woven, and
  iii) removing the at least one porogen from the electrospun porogen-containing non-woven obtained in method step ii) to obtain an electrospun porous non-woven.

The electrospinning of the at least one fibre polymer in method step ii) may preferably be carried out at a voltage of 6 kV to 25 kV, in particular 8 to 10 kV, more particularly 10 to 20 kV. The relative humidity (at room temperature) during electrospinning may preferably be from 10 to 90%, in particular from 20 to 80%, in particular from 25 to 40%, in particular adjusted in this way.

Additional polymers for electrospinning the at least one fibre polymer in method step ii) may, in a preferred embodiment, be electrospun simultaneously and/or alternately via separate nozzles or cannulas with suitable positioning. Furthermore, additional polymers may be dissolved directly in the solution of the at least one fibre polymer in method step ii) and spun as a polymer blend.

The removal of the porogen can preferably be carried out by dissolving in suitable solvents, in particular water, organic solvents, for example alcohols, in particular ethanol, or in particular physiological solutions, in particular PBS.

The removal of the porogen can preferably also be carried out by biodegradation and/or bioresorption in vitro or in vivo.

In a particularly preferred embodiment of the present invention, it is provided that in method step ii) the at least one porogen is electro-co-spun with the at least one fibre polymer or added to the at least one fibre polymer by electrospraying during electrospinning In a particularly preferred embodiment, method step ii) is carried out as electro-co-spinning the at least one porogen with the at least one fibre polymer to obtain an electro-spun porogen-containing non-woven.

In another preferred embodiment of the present invention, method step ii) is carried out as adding the at least one porogen in the form of electrospraying during electrospinning of the at least one fibre polymer to obtain an electro-spun porogen-containing non-woven.

In another preferred embodiment of the present invention, it is provided that method step ii) is carried out as discontinuous electrospinning of the at least one fibre polymer, having at least one interruption and at least two phases. In this case, the at least one porogen is added in at least one interruption of the electrospinning, i.e. between at least two phases of the discontinuous electrospinning Accordingly, in a preferred embodiment, method step ii) is carried out discontinuously in at least two phases and the adding of at least one porogen takes place between individual phases of the electrospinning.

In a preferred embodiment according to the invention, in method step i) the at least one porogen is provided in fibre form and/or in particle form and is added to the at least one fibre polymer in method step ii).

In a preferred embodiment according to the invention, the porogen is a porogen polymer or a porogen mineral salt, in particular sodium chloride.

In a preferred embodiment according to the invention, the porogen polymer is a water-soluble polymer, in particular PVP (polyvinylpyrrolidone) or PEG (polyethylene glycol), or an inorganic-organic hybrid material, in particular a titanium-oxo-carboxo complex.

In a preferred embodiment according to the invention, the implant according to the invention is producible by the method steps of x) providing an implant element, at least one adhesive system and at least one three-dimensional porous structural element made of at least one synthetic polymer, and y) at least partially contacting and attaching the three-dimensional porous structural element by means of the adhesive system to the implant element to obtain the implant.

In a particularly preferred embodiment, the implant according to the invention producible in this way is characterised in that the three-dimensional porous structural element provided in method step x) is a porous non-woven obtained by electrospinning at least one fibre polymer with the adding of at least one porogen and subsequent removal of the porogen from the fibre polymer.

In a preferred embodiment according to the invention, the implant is producible by the method steps of a) providing at least one porogen, one implant element, at least one adhesive system and at least one synthetic fibre polymer, b) electrospinning the at least one fibre polymer while adding the at least one porogen to obtain an electrospun porogen-containing non-woven, c) at least partially contacting and attaching the at least one non-woven to the implant element by means of the adhesive system; and d) removing the at least one porogen from the non-woven.

In a particularly preferred embodiment, method step c) can be carried out before method step d) and the implant can be obtained in method step d).

In a particularly preferred embodiment, method step c) may be carried out such that the at least partial contacting and attaching of the non-woven by means of the adhesive system is carried out using the electrospun porogen-containing non-woven obtained in method step b) and subsequently, in method step d), the at least one porogen added to the at least one fibrous polymer in method step b) is removed.

In a further preferred embodiment, method step c) may be carried out after method step d) and the implant may be obtained in method step c).

In a further preferred embodiment, it may be provided that the method of the invention provides that method step d) is carried out before method step c), that is, that the removal of the at least one porogen from the non-woven is carried out using the electrospun porogen-containing non-woven obtained in method step b) and, after removal of the at least one porogen from the electrospun porogen-containing non-woven, at least partial contacting and attaching of the at least one porous non-woven obtained in method step d) to the implant element is then carried out in method step c) by means of the adhesive system.

In a preferred embodiment according to the invention, the adhesive system comprises at least one inducibly polymerisable monomer, in particular HEMA (hydroxyethyl methacrylate), AEMA or METAC or a mixture of at least two of these monomers.

According to the invention, other monomers can also be used which polymerise via thermal, photocatalytic, catalyst-triggered, click chemistry or SIPGP. In particular, monomers are preferably used according to the invention which have at least one of the following functional groups: Acrylate, methacrylate, vinyl, norbornene, thiol, azide, alkyne, alkene, amine, hydroxy, carboxylate, thiol, isocyanate, cyanine, nitrile, anhydride, styrene or ester group.

In a particularly preferred embodiment of the present invention, the adhesive system comprises a mixture of HEMA and METAC, in particular a mixture in a ratio of 10 to 1 (wt. %).

In a particularly preferred embodiment of the present invention, the at least one fibre polymer may be dissolved in an organic solvent, in particular 1,1,1,3,3,3-hexafluoro-2-propanol or ethanol.

In a particularly preferred embodiment of the present invention, the adhesive system comprises, in addition to the at least one inducibly polymerisable monomer, at least one component selected from the group consisting of crosslinking component, viscosity modulator, radical initiator, cell adhesion enhancer and linker molecules.

In a particularly preferred embodiment of the present invention, in addition to the inducibly polymerisable monomer, the adhesive system may also have at least one cross-linking component, for example multi-armed and star-shaped oligomers or inorganic-organic hybrid materials, in particular titanium(IV) bis(ammonium lactate) dihydroxide, titanium oxo-alkoxo-carboxo clusters, carboxylate-coordinated zirconium alkoxides, alkoxysilanes or organically modified silanes.

In another preferred embodiment of the present invention, the adhesive system may have at least one viscosity modulator, for example HEMA polymers, in particular PEG or PVP, especially those with a chain length of 30000 to 50000.

In a particularly preferred embodiment of the present invention, at least one viscosity modulator may be present in a weight ratio of 20 to 30 wt. % in the adhesive system used according to the invention.

In a further preferred embodiment of the present invention, radical initiators, in particular catalysts, may also be present and used in the adhesive system used according to the invention. Accordingly, in a particularly preferred embodiment, it is provided that the at least one adhesive system have radical initiators such as azoisobutyronitrile, dibenzoyl peroxide, camphorquinone or inorganic peroxides.

Furthermore, the adhesive system preferably used according to the invention may be designed in such a way that polymerisation takes place via click chemistry.

In a preferred embodiment, amines, in particular in the form of AEMA (aminoethyl methacrylate), may be present in the adhesive system, in particular to improve cell adhesion to the implant element.

In a preferred embodiment, especially when metallic implant elements are used, linker molecules, especially bisphosphonates, may be present in the adhesive system, preferably those that can form ionic bonds with the surface of the implant element, especially the metallic implant element, and participate in the adhesion and contacting.

In a preferred embodiment according to the invention, the implant is a transcutaneous, percutaneous or perdermal implant, in particular a transcutaneous implant.

In a preferred embodiment according to the invention, the implant is a catheter, a fixator, a trichotomic instrument, an endo-exo prosthesis, in particular a transcutaneous osseointegrated prosthesis, an artificial bowel outlet, a percutaneous endoscopic gastrostomic device, a percutaneous endoscopic jejunostomy device, a bone conduction hearing apparatus, a CAPD catheter, in particular for peritoneal dialysis, a retroauricular fixed port for haemadialysis, a PEG probe, a transcutaneous sensor or a transcutaneous electronic device, in particular for nerve stimulation.

The present invention also relates to a method for preparing an implant, comprising the method steps of x) providing at least one three-dimensional porous structural element of at least one synthetic polymer, an implant element and at least one adhesive system; and y) at least partially contacting and attaching the at least one three-dimensional porous structural element by means of the adhesive system to the implant element to obtain the implant.

In a preferred embodiment according to the invention, an active agent, in particular an antibiotic active agent, is additionally provided in method step x).

In a particularly preferred embodiment, in method step y) the at least one active agent, in particular antibiotic active agent, is brought into contact with the at least one three-dimensional porous structural element and/or the adhesive system and is attached to the implant element.

In a particularly preferred embodiment, following method step y), in a method step z), cells of at least one cell type, in particular dermal fibroblasts and/or keratinocytes, in particular human dermal fibroblasts and/or human keratinocytes, are introduced, in particular seeded and cultivated, onto the at least one porous three-dimensional structural element attached to the implant element, and a cell-containing implant is obtained. This method is preferably an in vitro method.

In a preferred embodiment according to the invention, the invention also relates to an implant producible by a method according to method steps x) and y), in particular x) and y) and z).

In a particularly preferred embodiment of the present invention, an aforementioned method for producing an implant is provided, wherein the three-dimensional porous structural element provided in method step x) is formed as an electrospun porous non-woven and is producible by electrospinning with adding of at least one porogen and removal of the porogen.

The present invention therefore also comprises, in particular, a method for preparing an implant comprising the method steps of a) providing at least one porogen, an implant element, at least one adhesive system and at least one synthetic fibre polymer, b) electrospinning the at least one porogen while adding the at least one porogen to obtain an electrospun porogen-containing non-woven; and c) at least partially contacting and attaching the at least one non-woven to the implant element by means of the adhesive system; and d) removing the at least one porogen from the non-woven.

In a particularly preferred embodiment, method step c) can be carried out before method step d) or method step d) can be carried out before method step c).

In a particularly preferred embodiment, method step c) is carried out before method step d), i.e. the method comprises method steps a), b), c) and d) in the indicated temporal order, wherein the implant is obtained in step d).

In a further preferred embodiment of the present invention, a method for preparing an implant is also provided, wherein the method steps a), b), c), d) are carried out in the temporal order a), b), d) and c), wherein in step c) the implant is obtained.

In a preferred embodiment according to the invention, an active agent, in particular an antibiotic active agent, is additionally provided in method step a).

In a preferred embodiment according to the invention, the at least one active agent, in particular antibiotic active agent, is electrospun together with the at least one fibre polymer in method step b) and/or the implant obtained in method step d) is loaded, incubated or impregnated with the at least one active agent.

In a preferred embodiment according to the invention, following method step d), in a method step e), cells of at least one cell type, in particular dermal fibroblasts and/or keratinocytes, in particular human dermal fibroblasts and/or human keratinocytes, are cultivated on the at least one electrospun porous non-woven attached to the implant element and a cell-containing implant is obtained, on which, in a preferred embodiment, tissue or tissue layers, for example an epidermis, can be built up. In a preferred embodiment, this method is an in vitro method.

In a particularly preferred embodiment, the attaching of the at least one non-woven by means of the adhesive system to the implant element is carried out in such a way that regions of the porous structural element, in particular of the porous non-woven, which are intended for the integration of cells, are not filled by polymerisation of the inducibly polymerisable monomer, in particular HEMA, during or after use of the adhesive system.

In a particularly preferred embodiment, the non-woven attached to the implant element has both pores not filled with the adhesive polymer and pores filled with the adhesive polymer. Preferably, the pores filled with the adhesive polymer are located in the contact area, in particular the adhesion surface, between the implant element and the non-woven, in particular not on the surface of the porous implant. Preferably, the pores not filled with the adhesive polymer are located in the areas of the porous non-woven facing away from the implant element, in particular their surface, in particular on its surface of the implant.

In a particularly preferred embodiment, the attaching by means of the at least one adhesive system may be carried out in at least two phases, in particular multiple phases, each resulting in at least two layers, in particular multiple layers. In this way, the largest possible adhesion surface of the at least one porous structural element to the implant element is created and maximum contact integration and thus also anchoring volume in the tissue is achieved.

In a particularly preferred embodiment of the present invention, the adhesive system according to method steps x) and a) may also have at least one crosslinking component in addition to the inducibly polymerisable monomer, for example star-shaped oligomers or inorganic-organic hybrid materials, in particular titanium-oxo-alkoxo-carboxo clusters. The use of at least one crosslinking component advantageously leads, without being bound to the theory, to an increased three-dimensionality of the adhesive site, which ensures increased adhesion and/or bacteria-tight attachment of the at least one porous structural element, in particular the electrospun porous non-woven, to the implant element.

In a preferred embodiment according to the invention, the at least one active agent according to method steps x) and a), the at least one adhesive polymer and/or the at least one synthetic polymer has an antiproliferative, anti-inflammatory, antimigrative, antiphlogistic, antiangiogenic, cytostatic, antirestenotic, antineoplastic, antibacterial and/or antifungal effect.

In a preferred embodiment, the at least one active agent is in particular streptomycin, penicillin, vancomycin or gentamycin.

In a preferred embodiment according to the invention, in the method according to the invention, the attaching in method step y) and c) is carried out in the form of a polymerisation, in particular an induced polymerisation, in particular a "self-initiated surfaces photo polymerisation and photographting" (SIPGP), a thermally induced radical polymerisation or a light-induced radical polymerisation.

In a preferred embodiment according to the invention, the present invention also relates to an implant producible by a method according to method steps a) to d), in particular method steps a) to e).

The present invention also relates to a method for inserting an implant according to the invention into the human or animal body, in particular for therapeutic, cosmetic or nutritional purposes.

The invention also relates to the use of the implant according to the invention for the treatment and/or diagnosis of the human or animal body.

There are various ways of using the implant according to the invention.

In a preferred embodiment of the invention, the implant is used as a medical device, whereby the product is implanted in the patient in a cell-free manner. In this case, the biological attachment in the dermis, as well as the bacteria-tight seal through the epidermis, is preferably effected solely by the patient's self-healing forces.

In a further preferred embodiment of the invention, the application of the implant, in particular as an ATMP (advanced therapy medicinal product), takes place whereby the implant is first colonised with, for example, autologous or allogeneic cells, for example fibroblasts and keratinocytes, for example of the patient, and then implanted as a cell-containing implant. This method significantly accelerates the healing process.

Another preferred embodiment of the invention combines the application as a cell-free implant (medical device) and cellular implant. In this case, the cell-free implant (medical device) is implanted first and then autologous or allogeneic cells are introduced onto/into the implant, for example via a spray, whereby, for example, allogeneic fibroblasts and keratinocytes can be applied.

In the context of the present invention, the term "nanofibre" is understood to mean a fibre with a filament diameter <1000 nm, in particular a diameter in a range from 100 to 1000 nm, more particularly 100 to 900 nm, more particularly 200 to 800 nm.

In a particularly preferred embodiment, a "fibre polymer" is understood to mean a polymer suitable for forming a fibre, in particular a nanofibre.

In the context of the present invention, the term "biodegradable" is understood to mean that the element in question, in particular substance, in particular polymer, can be degraded by biological processes, in particular naturally occurring biological processes, in particular naturally occurring biological processes in a human or animal body, and thus loses its structural and/or material integrity.

In the context of the present invention, an "implant site" is understood to be the location on or in the body of the implant recipient into which the implant according to the invention is implanted.

In the context of the present invention, an "implant recipient" is understood to be a human or animal organism, in particular a living organism, which requires an implant for therapeutic, diagnostic, cosmetic, nutritional, lifestyle or other considerations.

In the context of the present invention, the term "synthetic polymer" is understood to mean that the polymer has been prepared using at least one artificial step and differs from naturally occurring polymers by virtue of this at least one artificial step, in particular a polymer has been prepared in an artificial system which does not occur naturally and/or using at least one component, in particular substance, which is present in a system which does not occur naturally.

In the context of the present invention, the term "synthetic fibre polymer" is understood to mean that the polymer is suitable for forming a fibre and has been prepared using at least one artificial step and is different from naturally occurring polymers by virtue of the at least one artificial step, in particular a polymer prepared in an artificial, non-naturally occurring system and/or using at least one component, in particular substance, present in a naturally non-occurring system.

In the context of the present invention, the term "irreversibly attached" is understood to mean that the physical connection between the implant element and the at least one porous structural element provided according to the invention is not detachable while maintaining the integrity of the implant and the elements of the implant, in particular the porous structural element and the implant element. An "irreversible attachment" is therefore particularly permanent, especially under biological conditions, in particular those occurring in human or animal living bodies.

In the context of the present invention, the term "laminar attached" is understood to mean that at least one laminar portion of a porous structural element formed as a three-dimensional laminar structure, in particular porous fibrous non-woven, is in contact with and attached to a laminar portion of a surface of an implant element, in particular attached by means of an adhesive system, in particular an adhesive polymer, in particular adhered.

In the context of the present invention, the term "three-dimensional whole skin model" is understood to mean an implant element attached via at least one adhesive polymer to at least one porous structural element of the present invention, in particular an electrospun porous non-woven made of nanofibres of at least one synthetic fibre polymer of the present invention, which has cells of at least one cell type, which have a differentiation into at least one tissue, in particular several tissues, in particular different tissue layers, in particular an epidermal and/or subepidermal skin layer, wherein the whole skin model in a particularly preferred embodiment corresponds to a naturally occurring skin and wherein in a preferred embodiment the cells are embedded in an extracellular matrix.

In the context of the present invention, the term a "phase" of a discontinuous electrospinning process is understood to mean temporal sections of electrospinning characterised by interruptions separating these temporal sections of electrospinning In the context of the present invention, the term "electrospun porous non-woven" is understood to be synonymous with the term "electrospun porous non-woven of nanofibres of at least one synthetic fibre polymer".

The methods according to the invention are characterised by a sequence of method steps i), ii) and iii) or x) and y) and optionally z), or a), b), c) and d) and optionally e). In a particularly preferred embodiment, the method steps take place in the order indicated in the present disclosure, unless otherwise indicated or apparent from expert knowledge.

In a particularly preferred embodiment of the present invention, it is provided that no further method steps are carried out between the individual explicitly indicated method steps.

Further preferred embodiments of the present invention will be apparent from the subclaims.

The invention will be explained in more detail below with reference to the examples and the accompanying figures.

The figures show:

FIG. 1: (A) Positioning of the porous non-woven according to the invention on the transcutaneous implant element. The arrows illustrate the orientation of the non-woven on the transcutaneous implant element. (B) The implant element—tissue interaction surface can be increased by adding another non-woven from below. The non-woven is physiologically integrated into the dermis (above the subcutis) and an epidermis over the non-woven seals the implant connection against bacteria.

Figure 2:
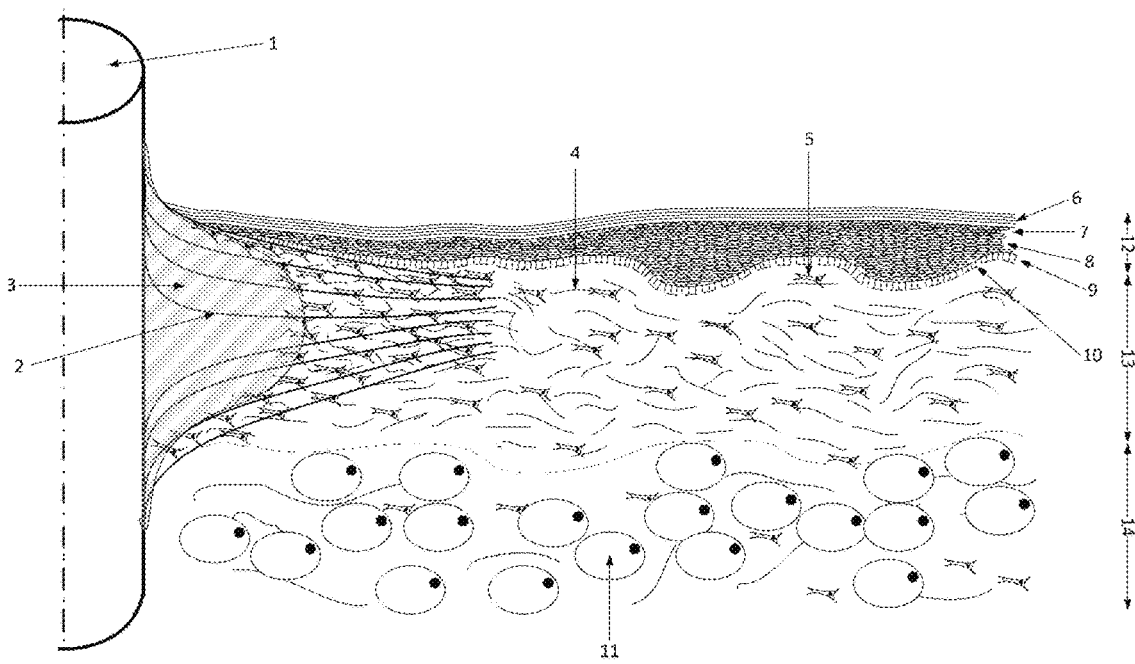

FIG. 2: Detailed and functional illustration of the attachment between the transcutaneous implant of the invention and the cutaneous tissue. (1) transcutaneous implant element; (2) continuous lines starting from the implant element represent the porous nanofibre non-wovens according to the invention; (3) grey area represents the area of adhesion; (4) thin short lines represent collagen or other proteins of the connective tissue; (5) fibroblast or other tissue cell; (6) stratum corneum; (7) stratum granulosum; (8) stratum spinosum; (9) stratum basale; (10) basement membrane; (11) adipocyte; (12) epidermis; (13) dermis; (14) subcutis.

Figure 3:
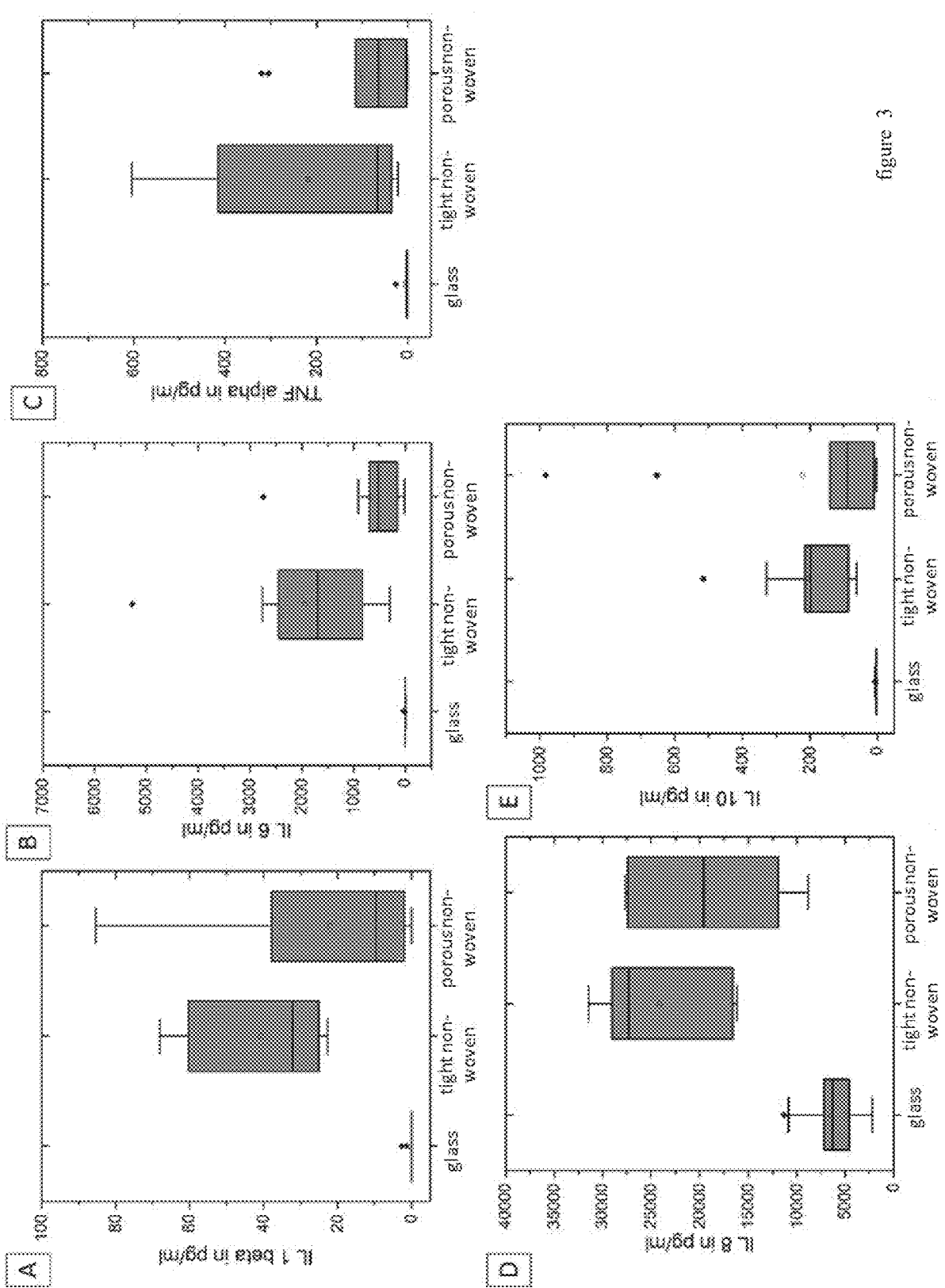

FIG. 3: Measurement of some cytokines from primary human macrophages after 48 hours of incubation. The material used was a dense nanofibre non-woven made of polyamide (control), a porous nanofibre non-woven according to the invention made of polyamide and a glass petri dish as inert control. The following cytokines were measured: (A) interleukin 1 beta; (B) interleukin 6; (C) TNF alpha; (D) interleukin 8 and (E) interleukin 10.

Figure 4:

FIG. 4: (A) The injury of a skin equivalent can be healed by inserting the porous non-woven according to the invention, thus showing the integration ability of the non-woven in vitro. (B) In addition to integration into skin models, the non-woven according to the invention can also serve as a substrate for the preparation of skin equivalents.

Figure 5:
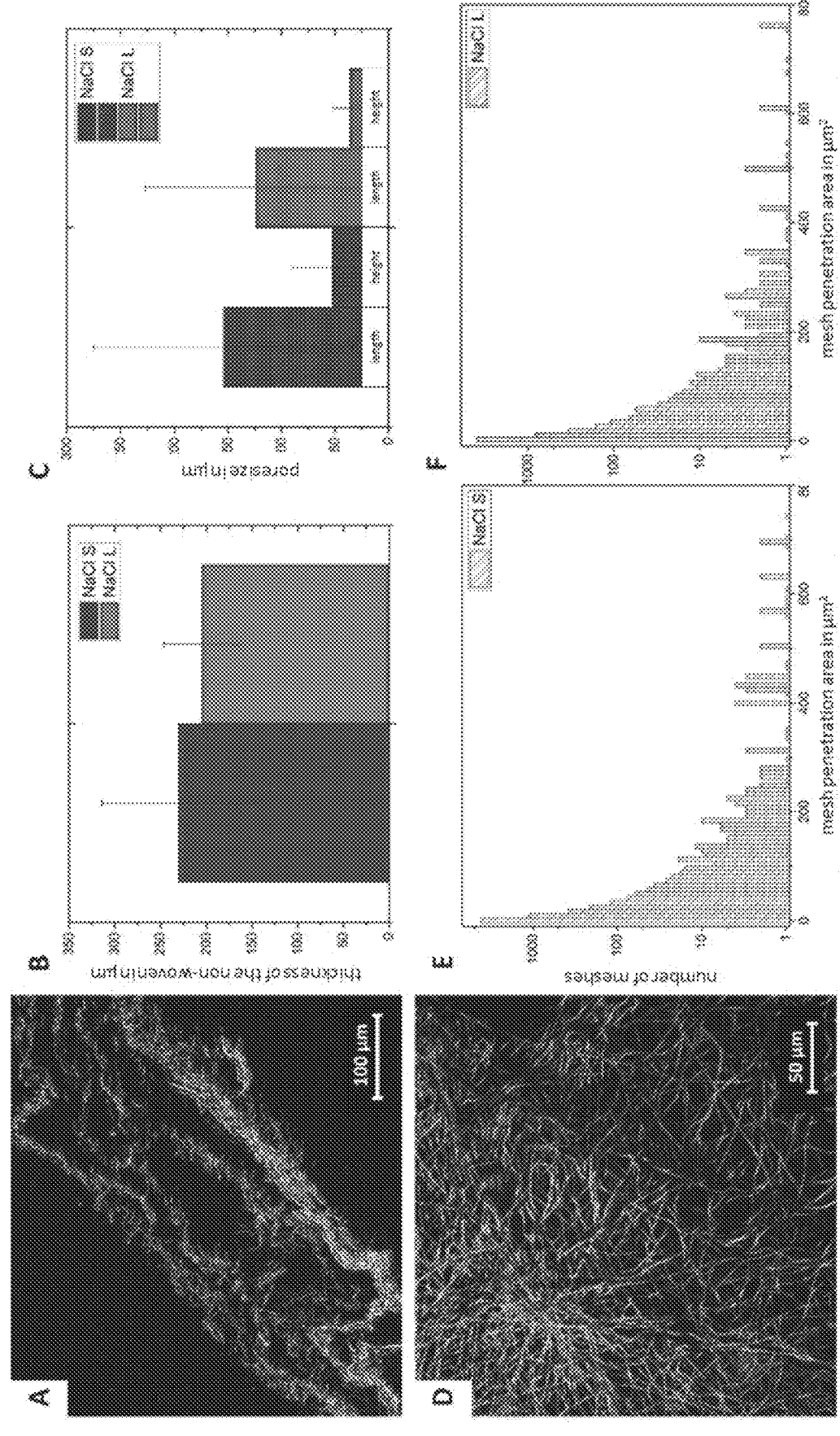

FIG. 5: Structural properties of the porous non-woven according to the invention. (A) Light microscope image of a paraffin section of the non-woven. Determination of the thickness of the non-woven in $\mu$m (B) and pore size in $\mu$m (C) through the cross-sections. (D) Confocal reflectance microscope image of the fibre structure. (E, F) Determination of the mesh penetration areas between the individual fibres.

Figure 6:
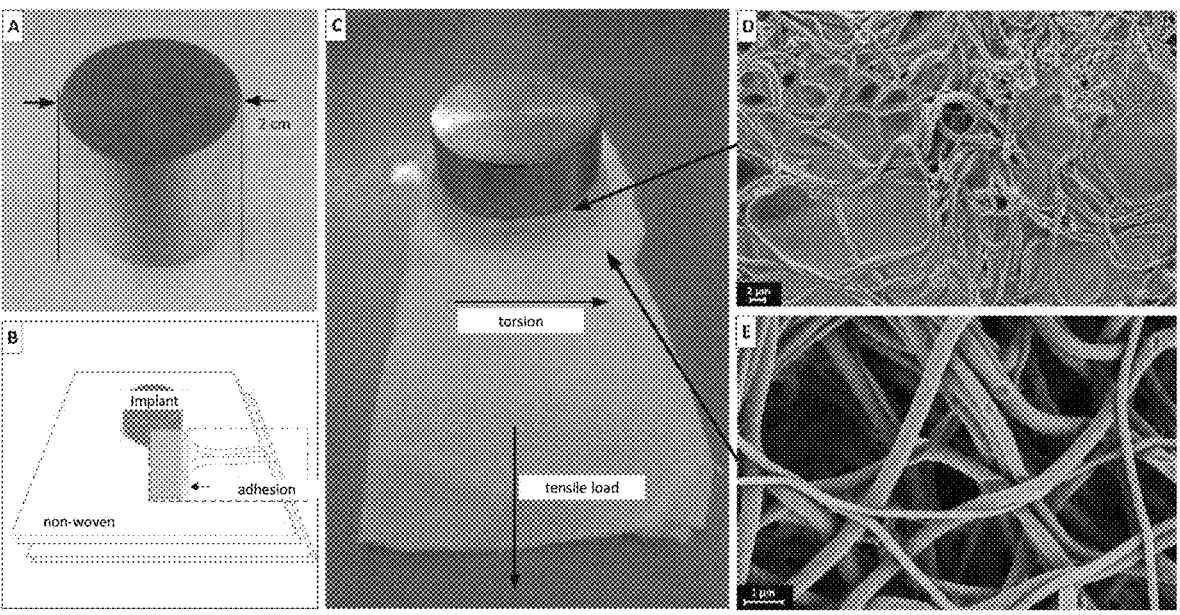

FIG. 6: Adhesion of the porous non-woven according to the invention to a metal specimen (implant element). (A) Cylindrical metal specimen with a diameter of 2 cm. (B) Schematic representation of the adhesion of four non-woven according to the invention to the specimen. (C) Photograph of the adhesion non-woven to the test specimen. SEM images of the adhesion with embedded fibres (D) and the area without adhesion (E).

Figure 7:
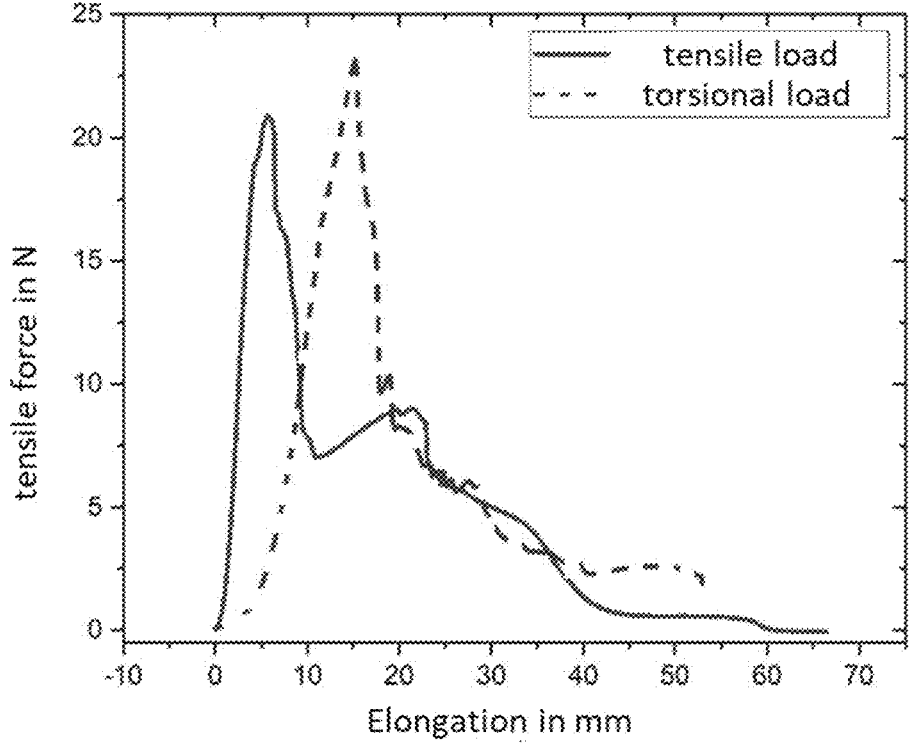

FIG. 7: Measurement of the maximum force loading of the adhesion in tension and torsion. The load directions are shown in FIG. 6C.

Figure 8:
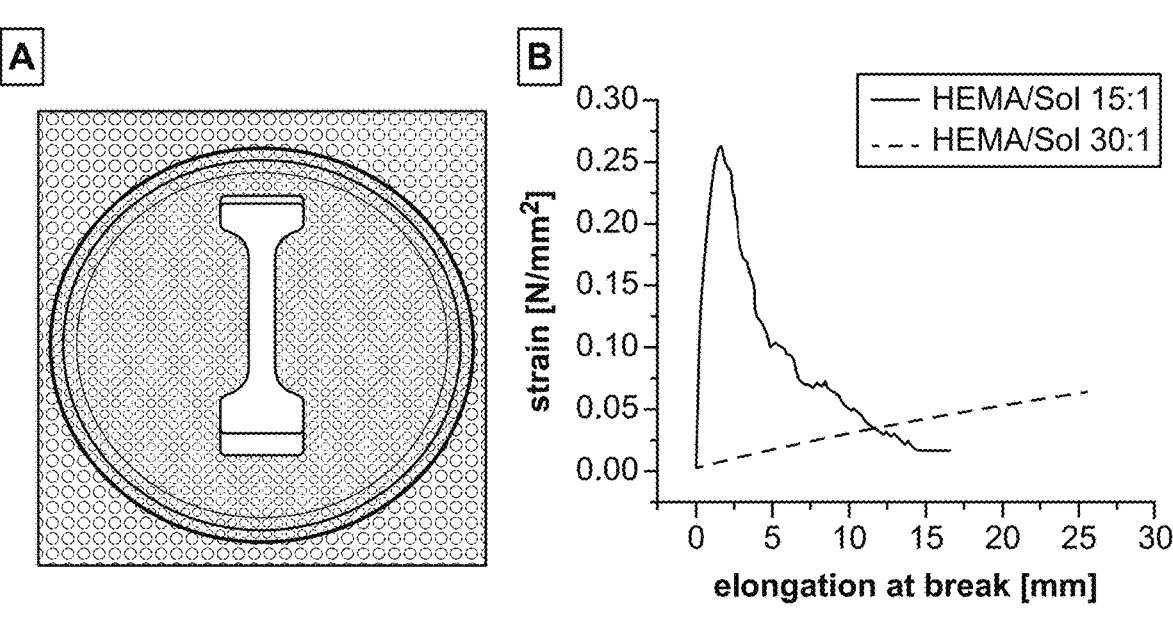

FIG. 8: Example of the modification of the monomer mixture. (A) Photograph of a tensile specimen of the polymerised adhesive material. (B) Example of a tensile measurement of the adhesive polymer. Mixtures of HEMA and cross-linker (inorganic-organic titanium-oxo-alkoxo-carboxo clusters) in volume ratio 15:1 and 30:1.

Figure 9:
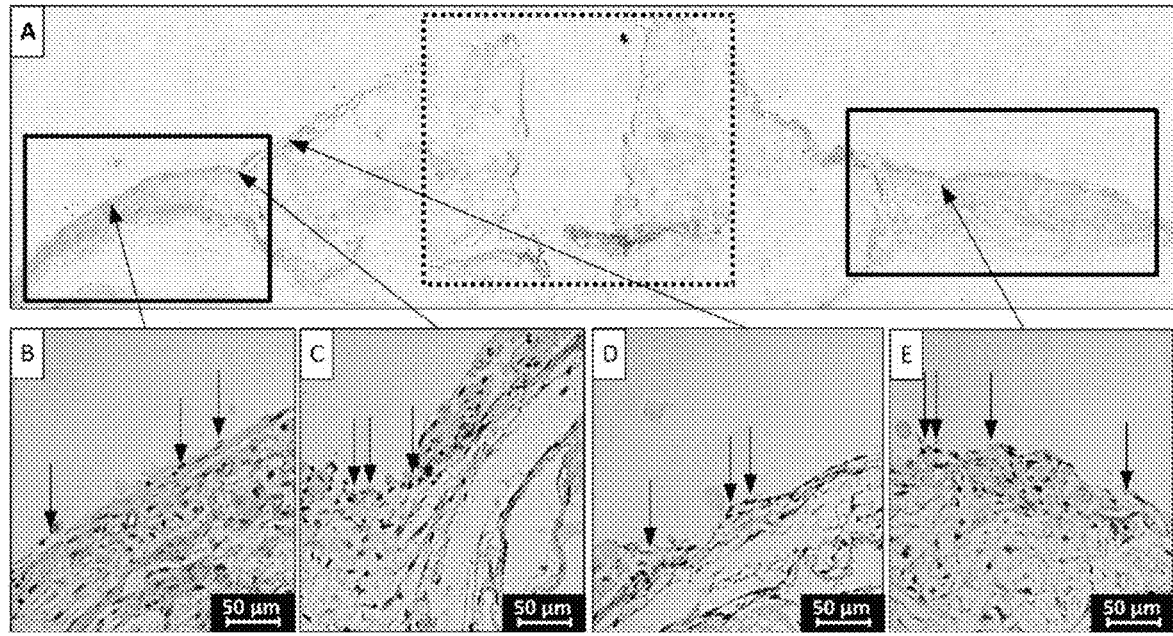

FIG. 9: Testing of bacterial interaction (in vitro) of a miniaturised transcutaneous implant. (A) Overview image of the entire implant: Recess in the centre represents the position of the implant. The material framed by interruptions around the recess is the adhesive material with enclosed fibres. The non-woven, which has been colonised with fibroblasts, is shown framed throughout. Figures (B-E) show isolated bacteria found (arrows).

EXAMPLES

Example 1

Electrospun Porous Non-Woven Method 1

Flexible and plastically deformable synthetic polymers are provided according to method step a). A solution of polyamide 6 (PA 6) dissolved in 1,1,1,3,3,3-hexafluoro-2-propanol at a concentration of 12% (m/v) was used. The polymer solution is transferred into a syringe and fitted with a metallic cannula. Two of these syringes are each installed in a syringe pump in the electrospinner and a flow rate of 0.55 ml/h is set. The distance between the tip of the cannula and the rotating collector (diameter: 33 cm) is moved to 15 cm and then the cannulae are connected to a high-voltage source. Further parameters of the spin process are a voltage of 8-10 kV at the cannulas, a relative humidity of 30% and a rotation of the collector of 100 rpm. After 3-5 minutes, the spinning process is stopped, the surface is moistened with ethanol and then sprinkled with NaCl particles as porogen according to method step b). This sequence is repeated 30 times until the non-woven is finished. The influence of the NaCl particle size on the structure of the non-woven is only slight (FIG. 5: particle diameter NaCl L (L: Large): 80-125 $\mu$m; NaCl S (S: Small): 1-80 $\mu$m). The particles are then released from the non-woven with water or PBS according to step d). A partial contacting and attaching of the thus obtained porous non-woven according to method step c) by means of an adhesive system with the implant element can be carried out according to example 3 to 6 before or after step d), in particular before step d).

Example 2

Electrospun Porous Non-Woven Method 2

Instead of manually applying the NaCl particles as porogen according to method step b), polymers are provided and used as porogen in this method. These can be simultaneously incorporated between the fibre polymer by electrospinning in the form of fibres or via electrospraying in the form of particles. Water-soluble polymers, in particular PVP or PEG, serve as porogen material. Furthermore, inorganic-organic hybrid materials can also be used, which are based in particular on titanium-oxo-carboxo complexes.

For electrospinning polymer fibres as porogen, a solution of PVP in ethanol with a concentration of 30% (m/v) is used. In the electro-co-spinning process with, for example, PA6

(Example 1), a distance of 15 cm and a voltage of 8-10 kV can also be set. This method can be carried out as a continuous spinning process over a duration of 3 h. Furthermore, this method can also be combined with a manual addition of NaCl particles (example 1) as a discontinuous process.

For electrospinning polymer particles as porogen, concentrations of 8-20% (m/v) and voltages of 10-20 kV are applied in the case of PVP. These parameters can be varied depending on the desired particle size (porogen size).

Removal of the porogens from Example 2 after the spinning process is done by dissolving in water, PBS (or other physiological salt solutions) or ethanol.

Example 3

Section Contacting the Implant Element with the Porous Non-Woven (Adhesion) According to Method Step c)

Since the non-woven cannot maintain bacteria-tight contact with the implant when force is applied, adhesion of the two components is required according to the invention. In a preferred embodiment, the mechanical characteristic values of the adhesion, such as modulus of elasticity or tensile strength, should preferably not be significantly lower than those of the fibres. If this is not the case, the forces and strains that occur may not be absorbed by the fibres and a predetermined breaking point could form in the adhesion. This attachment is preferably achieved by UV-triggered polymerisation. After providing the at least one porogen and at least one synthetic fibre polymer according to step a), and subsequent electrospinning according to step b) (see examples 1 and 2), the contacting and attaching of the implant element to the non-woven is carried out according to step c). The porous non-woven is provided with a hole that has a smaller diameter than the implant. The implant is then pushed through the hole in the porous non-woven to the adhesive position. Due to the difference in diameter, the porous material is stretched at the contact point and a parallel contact surface is formed between the porous non-woven and the implant. The liquid monomer of the adhesive system is then applied to the adhesion site using a pipette. The adhesive system provided for this purpose, containing the monomer hydroxyethyl methacrylate (HEMA), can first penetrate into the pores of the non-woven. The subsequent polymerisation leads to curing and filling of the non-woven pores (FIG. 6). To prevent the outer area of the non-woven, which is intended for skin integration, from not polymerising, the UV exposure is locally limited by an aperture (FIGS. 2 and 6). The polymerisation mechanism used is either self-initiated surface photopolymerisation and photografting (SIPGP) or thermal or light-induced radical polymerisation by addition of radical initiators. Both embodiments offer the possibility of forming covalent bonds between implant and non-woven by cleavage of hydrogen atoms on the substrates. This enables a particularly durable and mechanically resilient adhesion. When using organic substrates (non-woven and implant element made of plastic), this covalent bond is directly applicable via the described polymerisation. In the case of metallic implant elements, linker molecules can preferably be used, which on the one hand form ionic bonds on the metal surface (bisphosphonates) and on the other hand can participate in the polymerisation. By coating implant elements with inert surfaces, such as TiN, with polymers or diamond-like carbon layers (DLC), particularly stable covalent bonds can preferably be achieved through these polymerisations. Preferably, a minimum value of 10 N for an implant with a diameter of 2 cm can be defined as a threshold value for a minimum load capacity. With the above-mentioned adhesion, a maximum force of more than 20 N under tensile and torsional load could be measured until the adhesion failed (FIG. 7).

Example 4

Adhesion Method 1

This method for contacting the implant element with the porous non-woven according to method step c) uses polymerisation via SIPGP. The advantage of this polymerisation is that radical-like states are generated directly in HEMA monomers by the UV radiation and these then polymerise. This means that the use of potentially toxic radical starters can preferably be dispensed with. In a preferred embodiment, the adhesion takes place in several phases, resulting in several layers, whereby first the adhesive surface on the implant is wetted with the monomer and can covalently bond to the surface through polymerisation. Then the non-woven is pushed onto the implant, wetted with the monomer at the relevant point and exposed by means of a UV lamp (example parameters: light output 150 mW/cm², duration 1.5 min) or UV laser. To completely fill the free spaces in the non-woven with PolyHEMA, the wetting and exposure step is repeated at least three times. Depending on the application time of the implant, a total of two or four non-wovens can be bonded to the implant element. In case of long exposure times, it is preferable to ensure suitable cooling, as otherwise damage may occur to the implant or the non-woven.

Example 5

Adhesion Method 2

For the radical polymerisation to contact the implant element with the porous non-woven according to method step c), a radical initiator is used in the adhesive system, for example dibenzoyl peroxide or camphorquinone. The advantages of this are an accelerated reaction time, higher degree of cross-linking and lower exposure intensity. This makes this method particularly suitable for UV- or temperature-sensitive materials, especially PCL as non-woven. Similar to method 1 according to example 4, the polymerisations are preferably to be carried out in at least two phases.

Example 6

Material Selection for Adhesion

The preferred adhesive monomer for contacting and attaching the implant element to the porous non-woven according to method step c) (adhesion) is HEMA, which polymerises to polyHEMA under UV light. The polymer formed is present only in unbranched molecular chains, which limits the mechanical properties. In contact with an aqueous environment, a hydrogel-like state of the adhesion is formed. An increase in the mechanical strength of this adhesion can preferably be achieved by cross-linking. In addition to HEMA monomers, further cross-linking molecules, in particular star-shaped oligomers or inorganic-organic multinuclear clusters, such as titanium-oxo-alkoxo-carboxo clusters, are preferably used in the adhesive system (FIG. 8).

Preferred crosslinking components based on titanium complexes are commercial solutions of titanium(IV)bis(ammonium lactato)dihydroxide or a synthesised sol consisting of titanium-alkoxo-carboxo clusters: 1) In this case, 1 mol titanium ethoxide is added to 5 mol ethanol and 0.15 to 1 mol lactic acid (as an 85% aqueous solution) is mixed at room temperature for at least 2 h. Subsequently, the sol is hydrolysed with 0.1 to 20 mol water under stirring for at least 2 h. The sol can be used concentrated, undiluted or diluted with ethanol for adhesion. 2) 1 mol titanium ethylate is put into 5 to 20 mol ethanol and then added with 0.15 to 1 mol methacrylic acid, mandelic acid, acetic acid, propionic acid, malic acid, citric acid or mixtures of the mentioned acids as powder and mixed for at least 2 h under refluxing. The resulting clear sol is then cooled to at least room temperature, in particular to at least <0° C., and hydrolysed with 0.1 to 1 mol water for at least 5 h. The respective sol can be used concentrated, undiluted or diluted with ethanol for adhesion.

Due to its high content of oxygen groups, the adhesion of cells to this material is limited in some cases. However, since it is desirable for the epidermis to seal as closely as possible to the implant, improving cell adhesion in a preferable manner may be desirable. By adding aminoethyl methacrylate (AEMA), depending on the proportion, amines can be incorporated into the polymer system and thus improve cell adhesion. The possibly comparatively low viscosity of the HEMA makes adhesion to the implant more difficult, which can preferably take place in a vertical state due to the geometry of the implant. In a preferred embodiment, HEMA-soluble polymers are dissolved in the monomer to increase the viscosity. In particular, PEG or PVP with chain lengths of 30000 to 50000 and a mass content in the monomer solution between 20% and 30% are used for this purpose. These solutions lead to a particularly effective adhesion, since on the one hand the local polymerisation can be improved and on the other hand the curing time can be reduced.

Example 7

Method of Preparing Skin Equivalent on Nanofibre Non-Wovens

The implant can be implanted cell-free or already colonised with cells in vitro. For example, for a cellular transcutaneous implant, the porous non-woven that has already been attached to the implant element can be colonised with fibroblasts. In addition, an epidermis can be built up on the fibroblast-populated non-woven in vitro. This method can produce a transcutaneous implant directly attached to a skin equivalent, which can thereby already be attached to skin in vitro. According to the invention, a skin model was constructed on the basis of the porous non-wovens.

For the preparation of the skin model according to method step e), after contacting and attaching the at least one non-woven to the implant element by means of the adhesive system and removing the porogen according to method step d), two porous non-wovens obtained according to the invention are clamped on top of each other in cell crowns. Then 30000 fibroblasts/cm² are sown on the non-woven. These are cultivated for two weeks and colonise the entire volume of the non-woven. Through the supplementation of ascorbic acid derivatives (e.g. ascorbic acid 2-phosphate; concentration: 500 µM), a natural stimulation of the synthesis of extracellular matrix takes place. These proteins are produced throughout the non-woven and thereby biologise the given nanofibre structure. This method makes it possible to generate a reconstructed human epidermis (rhE) on the biologised material in the subsequent step. For this purpose, 600000 keratinocytes/cm² are seeded on the biologised non-woven. A subsequent airlift culture is used to form a complete epidermis after 2-3 weeks of culture (adapted from Jannasch et al., Experimental Parasitology, 150, 22-30, 2015). Thus, according to the invention, a whole skin model based on the porous non-wovens is provided.

Example 8

Anchoring the Implant in the skin

After providing an implant element according to the invention and a non-woven according to method steps a) and b) (example 1 or 2), the non-woven is first laminar (parallel) adhered to the implant element (example 3, 4 or 5) and is oriented deeper by 90° radially outwards from the implant element (FIG. 1A; illustrated by arrows) (method step c)), then the at least one porogen is removed (method step d)). The advantages of this non-woven orientation are that, on the one hand, a large adhesion surface is created on the implant element and, on the other hand, that a maximum contact, integration and thus also anchoring volume in the skin tissue can be achieved. This process can also be repeated in a downward direction to increase the mechanical strength (FIG. 1B).

The porous structure of the non-woven enables integration and mechanical anchoring in the dermal part of the surrounding skin (FIG. 2). After implantation, the migration of cells into the non-woven from the surrounding dermal tissue (fibroblasts, macrophages, possibly endothelial cells) takes place in vivo. These colonise the non-woven and fill the pores with natural connective tissue. After this dermal integration (mechanical connection), the bacteria-tight seal takes place by forming an epidermis over the dermally integrated non-woven up to the implant element.

In order to be able to achieve integration into the dermis, a non-woven imitating the connective tissue was therefore developed in accordance with the present invention. After providing the at least one synthetic fibre polymer and at least one porogen according to step a), the nanofibres required therefor are generated via the method of electrospinning according to step b). During this process, the incorporation of particulate or fibrous porogens in the nanofiber non-woven takes place. The subsequent dissolving out of these porogens according to step d) creates a porous nanofibre non-woven, which enables the migration and colonisation of the body's own cells. On the one hand, this procedure reduces the inflammatory (FIG. 3) and foreign body reaction, and on the other hand, it enables the independent integration into the dermis. Depending on the duration of application (from weeks and months to many years), both biodegradable polymers, e.g. polyesters such as PCL, and permanently stable polymers, especially polyamides, can be used as polymers. The ability of these porous nanofibre non-wovens to integrate into skin tissue was demonstrated when wounded in vitro skin equivalents healed completely after insertion of the non-wovens (FIG. 4A). Another property of these non-wovens is that they can be used as a basic structure for the construction of in vitro skin equivalents (FIG. 4B).

Example 9

Addition of Active Agent

Until the epidermis forms a bacteria-tight seal with the implant, there is a risk of infection, which considerably impedes the healing process. Therefore, antibacterial properties of the material are desirable. This can be achieved in particular by incorporating antibiotic agents directly into the spinning solution and thus directly into the nanofibres during the spinning process. Another possibility is to incubate the finished implant in active agent solutions. The active agents are incorporated into the fibres and the adhesive material and can diffuse out after implantation.

Bacterial interaction with an implant colonised with fibroblasts was tested in a miniaturised model (implant diameter 2 mm). For this purpose, 4 porous polyamide non-wovens (preparation example 1) were adhered to an implant element designed as a metal pin (2 mm diameter) (according to example 4). Subsequently, 30000 fibroblasts/cm² were seeded on the non-woven that was adhered to the implant element. The culture period was initially 2 weeks (see example 7) in DMEM with the additions FCS (10% v/v), ascorbic acid 2-phosphate (500 μM) as well as penicillin and streptomycin. Subsequently, the medium was changed to antibiotic-free medium for 4 days in order to wash antibiotic residues from the cell-nanofibre composite, i.e. the implant. (FIG. 9). For the bacterial test, 108 CFU *Staphylococcus aureus* were placed on the non-woven implant and analysed after 24 hours. This showed that no bacteria could survive on or in the adhesive material (interrupted framed area, FIG. 9). The non-woven colonised with cells also showed the killing of almost all bacteria after 24 h (continuously framed area, FIG. 9).

The invention claimed is:

1. An implant comprising at least one three-dimensional porous structural element of at least one synthetic polymer, wherein the at least one porous structural element is irreversibly attached to an implant element by means of at least one adhesive polymer, wherein the at least one synthetic polymer is a synthetic fibre polymer selected from the group consisting of polyamide, polyacrylonitrile, polyolefins and poly-caprolactone (PCL) and wherein the at least one adhesive polymer is a cross-linked or non-cross-linked poly-hydroxyethyl methacrylate (poly-HEMA) polymerised [2-(methacryloyloxy)ethyl]trimethylammonium chloride (METAC), polymerised 2-aminoethyl methacrylate (AEMA) or a copolymer of at least two of the monomers HEMA, METAC or AEMA.

2. The implant according to claim 1, wherein the three-dimensional porous structural element is selected from the group consisting of electrospun porous non-woven of nanofibres of at least one synthetic fibre polymer, porous sponge, porous membrane and foamed porous polymer.

3. The implant according to claim 1, wherein the pore size of the porous structural element, in particular the electrospun porous non-woven fabric, is 0.1 μm to 800 μm, in particular 0.1 μm to 500 μm, in particular 0.5 μm to 300 μm.

4. The implant according to claim 1, wherein the porous structural element, in particular electrospun porous non-woven, has a thickness of 50 μm to 300 μm, in particular 100 μm to 250 μm, in particular 150 μm to 250 μm.

5. The implant according to claim 1, wherein the implant element is composed of an organic material, an inorganic material or an organic-inorganic hybrid material, in particular is an implant element made of plastic and/or metal, and/or a metal compound.

6. The implant according to claim 1, wherein the porous structural element, in particular electrospun porous non-woven, is cell-free.

7. The implant according to claim 1, wherein the porous structural element, in particular electrospun porous non-woven, has cells of at least one cell type, in particular dermal fibroblasts and/or keratinocytes, in particular human dermal fibroblasts and/or human keratinocytes.

8. The implant according to claim 1, wherein the implant is a three-dimensional whole skin model.

9. The implant according to claim 1, wherein the implant, in particular the porous structural element, in particular the electrospun porous non-woven, and/or the at least one adhesive polymer, has at least one active agent, in particular an antibiotic active agent.

10. The implant according to claim 2, wherein the electrospun porous non-woven is producible by
    i. Providing at least one porogen and at least one synthetic fibre polymer,
    ii. Electrospinning the at least one fibre polymer while adding the at least one porogen to obtain an electrospun porogen-containing non-woven; and
    iii. Removing the at least one porogen from the electrospun porogen-containing non-woven obtained in method step ii) to obtain an electrospun porous non-woven.

11. The implant of claim 10, wherein in process step ii) the at least one porogen is electrospun with the at least one fibre polymer or added to the at least one fibre polymer by electrospraying during electrospinning.

12. The implant according to claim 10, wherein the electrospinning in method step ii) is carried out discontinuously in at least two phases and the adding of at least one porogen takes place between individual phases of the electrospinning.

13. The implant according to claim 10, wherein in method step i) the at least one porogen is provided in fibre form and/or in particle form and in method step ii) is added to the at least one fibre polymer.

14. The implant according to claim 10, wherein the porogen is a porogen polymer or a porogen mineral salt.

15. The implant of claim 10, wherein the porogen polymer is a water-soluble polymer, in particular PVP (polyvinylpyrrolidone), PEG (polyethylene glycol) or an inorganic-organic hybrid material, in particular a titanium-oxo-carboxo complex.

* * * * *